United States Patent [19]
Hammond et al.

[11] Patent Number: 5,558,998
[45] Date of Patent: Sep. 24, 1996

[54] DNA FRAGMENT SIZING AND SORTING BY LASER-INDUCED FLUORESCENCE

[75] Inventors: Mark L. Hammond, Angier, N.C.; James H. Jett, Los Alamos, N.M.; Richard A. Keller, Los Alamos, N.M.; Babetta L. Marrone, Los Alamos, N.M.; John C. Martin, Los Alamos, N.M.

[73] Assignee: The Regents of the Univ. of California, Alameda, Calif.

[21] Appl. No.: 486,400

[22] Filed: Jun. 5, 1995

Related U.S. Application Data

[63] Continuation-in-part of Ser. No. 218,148, Mar. 24, 1994, abandoned, which is a continuation-in-part of Ser. No. 7,308, Jan. 21, 1993, abandoned, which is a continuation-in-part of Ser. No. 841,114, Feb. 25, 1992, abandoned.

[51] Int. Cl.$^6$ .......................... C12Q 1/68; G01N 33/483; G01N 35/08
[52] U.S. Cl. .................. 435/6; 436/52; 436/63
[58] Field of Search .................. 435/6; 436/52, 436/63

[56] References Cited

U.S. PATENT DOCUMENTS 3,710,933  1/1973  Fulwyler et al. ..................... 209/3.1

OTHER PUBLICATIONS

Cantor et al., *Biophysical Chemistry*, "Part III: The Behavior of Biological Macromolecules," pp. 1252–1255, (1942).
A. V. Carrano et al., "A High–Resolution, Fluorescence–Based, Semiautomated Method for DNA Fingerprinting", Genomics 4:129–136, (1989).
L. Scott Cram et al., "Fluorescence Polarization and Pulse Width Analysis of Chromosomes by a Flow System, " J. Histochem Cytochem, 27:445–453, (1979).
Z. Darzynkiewicz et al., *Methods in Cell Biology*, 33, Ch. 37, "Fluorescence *in Situ* Hybridization with DNA Probes," pp. 383–400, Academic Press, Inc., New York (1990).
J. H. Hahn et al., "Laser–Induced Fluorescence Detection of Rhodamine at 6×10$^{-15}$ M," Appl. Spectosc. 45:743, (1991).
Gray et al., "High Speed Chromosome Sorting," Science, 23:323 (1987).
K. Heine, "DNA on Trail, " Outlook 26:4, pp. 8–14, (1989).
Thomas M. Jovin, "Fluorescence Polarization and Energy Transfer: Theory and Application," *Flow Cytometry and Sorting*, Ed. M. R. Melamed et al., pp. 137, 156, John Wiley & Sons (1979).
J. B. LePecq et al., "A Fluorescent Complex Between Ethidium Bromide and Nucleic Acids," J. Mol. Bio., 27:87–106, (1967).
T. Lindmo et al., "Flow Sorters for Biological Cells," *Flow Cytometry and Sorting, Second Edition*, Ed. M. Melamed et al., John Wiley & Sons, pp. 145–169, (1990).
Rye et al., "Stable Fluorescent Complexes of Double–stranded DNA with Bis–intercalating Asymmetric Cyanine Dyes: Properties and Applications," Nucleic Acids Research, 20:2803 (1992).
J. Sambrook et al., "Digesting DNA with Restriction Enzymes, "*Molecular Cloning*, pp. 5.28–5.33, (1989), Cold Spring Harbor Laboratory Press (1989).
E. B. Shera et al., "Detection of Single Fluorescent Molecules, " Chem. Phys. Lett., 174:553–557, No. 6, (Nov. 23, 1990).
Steven A. Soper et al., "Single–Molecule Detection of Rhodamine 6G in Ethanolic Solutions Using Continuous Wave Laser Excitation, " Anal. Chem., 63:432–437, (1991).
J. I. Thornton, "DNA Profiling," C&EN, pp. 18–30, (Nov. 20, 1989).
Goodwin et al. (1993), Nucl. Acids Res. 21(4):803–806.
Gray et al. (1975), Proc. Nat. Acad. Sci. USA: 72(4): 1231–1234.
Gray et al. (1979), Chromosoma 73: 9–27.

*Primary Examiner*—Mindy Fleisher
*Assistant Examiner*—Philip W. Carter
*Attorney, Agent, or Firm*—Ray G. Wilson

[57] ABSTRACT

A method is provided for sizing DNA fragments using high speed detection systems, such as flow cytometry to determine unique characteristics of DNA pieces from a sample. In one characterization the DNA piece is fragmented at preselected sites to produce a plurality of DNA fragments. The DNA piece or the resulting DNA fragments are treated with a dye effective to stain stoichiometrically the DNA piece or the DNA fragments. The fluorescence from the dye in the stained fragments is then examined to generate an output functionally related to the number of nucleotides in each one of the DNA fragments. In one embodiment, the intensity of the fluorescence emissions from each fragment is linearly related to the fragment length. The distribution of DNA fragment sizes forms a characterization of the DNA piece for use in forensic and research applications.

12 Claims, 12 Drawing Sheets

DNA FRAGMENT SIZING AND SORTING BY LASER-INDUCED FLUORESCENCE

RELATED CASE

This is a continuation-in-part of application Ser. No. 08/218,148 filed on Mar. 24, 1994, abandoned, which is a continuation-in-part application Ser. No. 08/007,308 filed on Jan. 21, 1993, abandoned which is a continuation-in-part of U.S. Patent application Ser. No. 07/841,114, filed Feb. 25, 1992 now abandoned.

BACKGROUND OF THE INVENTION

This invention relates to DNA analysis and, more particularly, to DNA fragment size distribution analysis and sorting. This invention is the result of a contract with the Department of Energy (Contract No. W-7405-ENG-36).

The human genome is comprised of some three billion nucleotides forming the 22 pairs of autosomes plus 2 sex chromosomes, each with continuous DNA pieces of 50–500 million nucleotides. The organization and sequence of DNA forming the human genome contains unique information about the constitution of the organism that provides the DNA. One method for accessing this information is to fragment the DNA at known sites and then to analyze the distribution of fragment sizes, i.e., the number of nucleotides in each fragment between each of the sites. Polymorphisms in the genome structure among individuals lead to substantial variation in the fragment sizes obtained from fragmentation of DNA pieces and allow one to differentiate one person from another or to form a basis for assessing a person's susceptibility to genetic diseases. Analysis of these polymorphisms is often referred to as DNA fingerprinting.

DNA fingerprinting is an important medical diagnostic tool, with additional applications to forensic identification, medical genetics, monitoring the effects of environmental mutagens, basic molecular biology research, and any application that uses gel electrophoresis for DNA fragment sizing and separation. One form of DNA fingerprinting involves "restriction fragment length polymorphism" (RFLP) where restriction enzymes are used to cut a DNA piece from a specific source into shorter pieces, or fragments, of DNA. RFLP provides a unique pattern of DNA fragments containing a unique DNA sequence ordered by fragment size (the DNA fingerprint) when a DNA specimen is digested with restriction enzymes. There are many known restriction enzymes and each recognizes a specific DNA sequence of four to twelve base pairs at which it cuts the DNA, resulting in smaller fragments of DNA.

Once the DNA piece has been cut into many fragments, electrophoresis is conventionally used to separate the fragments by size. An electric field is placed across a gel (either in the form of a slab or packed into a small capillary column) containing the fragments causing the smaller fragments to move faster than the larger ones. Gel electrophoresis is a well known technique and has been used to produce band patterns of DNA fragments that form a fingerprint to identify the individual source of the DNA piece under analysis. The band patterns of specific DNA sequences are conventionally visualized by binding radioactive DNA probes to the separated DNA fragments and exposing suitable film to the radioactive labeled fragments. See, e.g., J. I. Thornton, "DNA Profiling," C&EN, pp. 18–30 (Nov. 20, 1989); K. Heine, "DNA on Trial," Outlook 26:4, pp. 8–14 (1989). In one variation, the fragment ends are tagged with a fluorescent dye so that the fragment migration time along a known path length in an electrophoretic gel can be determined by automated fluorescence detection. See, e.g., A. V. Carrano, "A High-Resolution, Fluorescence-Based, Semiautomated Method for DNA Fingerprinting," 4 Genomics, pp 129–136 (1989).

There are, however, several limitations on the use of gel electrophoresis, particularly where large fragment sizes and radioactive labeling are involved. In both instances, the electrophoretic separation process takes considerable time to provide resolution for large size fragments. The development of images from radioactive probes is an additional time consuming step and has health hazards and environmental concerns associated with radioactive materials. Additionally, the distribution of fragment sizes is logarithmic so that the separation, i.e., resolution between large fragments is less than for small fragments. Electrophoresis also requires relatively large amounts of DNA to obtain a recognizable pattern.

It is desirable to provide a DNA fragment size analysis technique that uses only small quantities of DNA (maybe only a single fragment), provides size information within a short time, and has a high base pair (bp) resolution between fragment sizes. These and other problems of the prior art are addressed by the present invention wherein flow cytometry-based techniques are used to obtain a distribution of DNA fragment sizes from a DNA piece.

Accordingly, it is an object of the present invention to provide rapid determination of DNA fragment sizes.

It is another object of the present invention to obtain a high resolution for sizing DNA fragments, particularly long fragments, i.e., greater than 10 kbp.

One other object of the present invention is to require only a small DNA sample to provide accurate DNA fragment size analysis.

Yet another object of the present invention is to enable fragment length detection without the use of radioactive labels.

A further object of the present invention is to use fluorescent intensities to determine the length of DNA fragments.

Still another object of the present invention is to use the sorting capabilities associated with flow cytometry to sort the fragments by size, i.e., length, for further study.

One other object of the present invention is to obtain an analysis of DNA fragments that is linearly related to the fragment sizes.

Another object of the present invention is to linearly quantitate the number of DNA fragments within any given size class.

It is an object of the present invention to provide an alternative to gel electrophoresis for DNA fragment length sizing.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method of this invention may comprise the use of an induced fluorescence to quantitate the length of DNA fragments of about 50 dbp or less. DNA fragments are obtained naturally or a piece of DNA is fragmented at known sites to produce a plurality of DNA fragments. All of the DNA fragments are treated with a dye effective to stain stoichiometrically the DNA fragments. The stained DNA fragments are then examined fluorescently to generate an output related functionally to the number of nucleotides in each one of the DNA fragments of about 50 kbp or less. In one output, the intensity of the fluorescence emissions from each fragment is linearly proportional to the fragment length.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION OF THE INVENTION

Figure 1A:
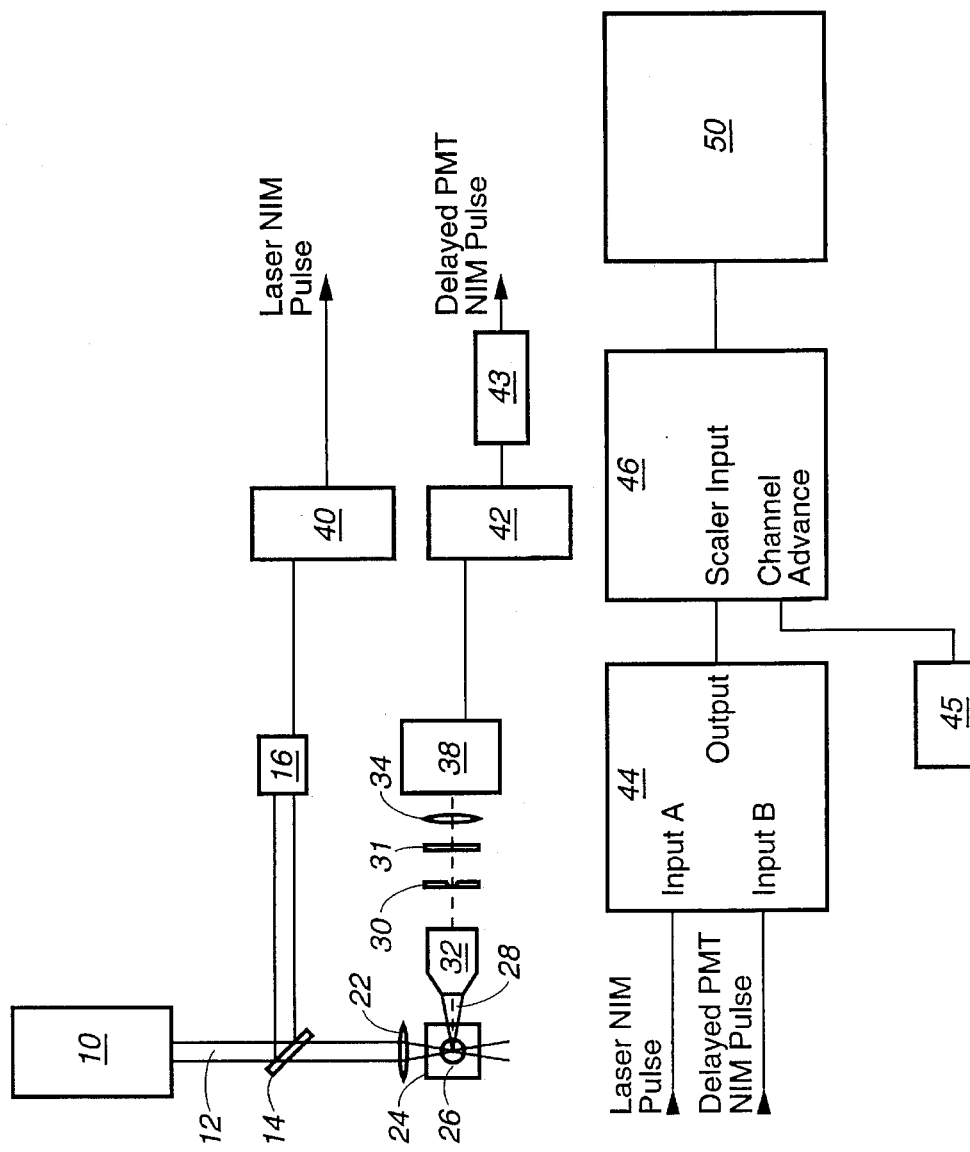
FIG. 1A is a block diagram schematic of apparatus for DNA sizing using pulsed laser excitation and time gated detection.

In accordance with the present invention, DNA fragments are characterized, i e., "fingerprinted," using flow cytometry-based techniques to provide a rapid analysis of DNA fragment sizes having a number of nucleotides of about 50 kbp or less obtained from natural events or by fragmenting a selected DNA piece with one or more enzymes selected to cleave DNA at known sequence sites. As used herein and in accordance with the example, the term "DNA" means double stranded DNA. One exemplary procedure for sizing is the following:

1. DNA fragments are provided from a naturally occurring source or by restriction enzyme digestion of a larger DNA piece at known locations to provide a solution of DNA fragments. The DNA fragments may be stained, i.e., labeled, stoichiometrically with an appropriate fluorescent dye before or after the DNA piece is fragmented.

2. The stained DNA fragments are passed through a detection apparatus at a concentration and rate effective to provide only one fragment in the fluorescence excitation and detection volume at any one time.

3. Each stained DNA fragment is excited, e.g., with laser irradiation, in the excitation volume and the resulting fluorescence intensity is measured, wherein the intensity of the induced fluorescence is a linear measure of the amount of stain bound to the fragment and, therefore, fragment length.

4. The number of fragments at each different intensity provides an analysis of the number of fragments of each length produced from the DNA piece by the selected enzyme or enzymes.

A DNA piece may be first selected from any suitable source, e.g., blood, tissue samples, semen, laboratory research specimens, etc. The DNA piece is then fragmented using a method appropriate for a particular application of the analysis. One particularly useful method is enzymatic cleavage using a restriction endonuclease that recognizes specific sites, i.e., specific nucleotide sequences, and cleaves the DNA piece within the identified sequence. For example, the enzyme Eco RI cuts at the double strand recognition site

... GAATTC...
...CTTAAG....

More than a hundred different restriction enzymes and their respective cleavage sites are known. It will be appreciated that identical DNA pieces from a single source might be digested with different enzymes to yield a family of fingerprints. Alternatively, a DNA piece may be digested with multiple enzymes to further particularize the fragment size distribution analysis.

Fragmentation, i.e., digestion, of a DNA piece with a selected enzyme is a well-known process, where the optimum digestion conditions are specified by the enzyme manufacturer. A generic restriction enzyme process for use with 0.2–1 μl g of DNA is given by J. Sambrook et al., *Molecular Cloning*, pp. 5.28–5.33, Cold Spring Harbor Laboratory Press (1989): 1. Place the DNA solution in a sterile microfuge tube and mix with sufficient water to give a volume of 18 μL. 2. Add 2 μL of an appropriate restriction enzyme digestion buffer and mix by tapping the tube. An exemplary buffer may be formed as follows:

200 mM potassium glutamate 50 mM Tris-acetate (pH 7.5)

20 mM magnesium acetate 100 μg/mL bovine serum albumin (Fraction V; Sigma)

1 mM β-mercaptoethanol.

3. Add 1–2 units of restriction enzyme and mix by tapping the tube, where 1 unit of enzyme is defined as the amount required to digest 1 μg of DNA to completion in 1 hour in the recommended buffer and at the recommended temperature in a 20-μL reaction.

4. Incubate the mixture at the appropriate temperature for the required period of time.

5. Stop the reaction by adding 0.5 M EDTA (pH 8.0) to a final concentration of 10 mM.

DNA can be fragmented by a variety of other techniques in addition to restriction enzyme digest:

1. DNase hypersensitivity sites (DNase footprinting). Chromatin digestion by DNase will produce fragments of various lengths due to differences in proteins that bind to the DNA and prevent cutting of the DNA by a DNase at sites where protein is bound (D. J. Galas et al., Nucleic Acids Res., 5:3157 (1987)).

2. RNase cleavage of single-base pair mismatches. A fluorescent RNA probe complementary to a normal, or wild type, DNA sequence of interest is synthesized. This complementary probe is then annealed to the target DNA that is to be analyzed. To determine if a single nucleotide mismatch exists between the fluorescent probe strand and the target DNA strand, the RNA:DNA hybrid is treated with RNase A. RNase A specifically cleaves single stranded regions of RNA, thus cleaving the single base pair mismatch region in the fluorescent RNA strand of the RNA:DNA hybrid. (See R. M. Myers et. al., Science 230:1242 (1985) and E. F. Winter et al., Proc. Natl. Acad. Sci. 82:7525 (1985)).

3. RecA-assisted restriction endonuclease cleavage. Short oligonucleotides coated with RecA protein are annealed to the complementary target DNA sequence. The DNA:oligonucleotide hybrid is treated with Eco RI methylase enzyme. Eco RI sites that are not protected by the oligonucleotide are methylated while oligonucleotide protected Eco RI sites remain unaffected. Eco RI restriction endonuclease will cleave only at protected sites (i.e., unmethylated). This method has been used to generate fragments>500,000 base pairs. (L. J. Ferrin, Science, 254:1494 (1991).

4. DNA fragmentation can also be accomplished by techniques other than enzyme digestion.

For example, ultrasonic excitation at selected frequencies might be used to produce a family of size distributions. Various chemicals also react with the nucleotides and may be used to fragment DNA pieces.

The DNA fragments are stained with a fluorescent dye for flow cytometric analysis. A fluorescent dye is selected to bind stoichiometrically to the DNA fragments and is preferably an intercalating dye. The complex may be formed in different ways, i.e., single stranded DNA, double stranded DNA, specific base pairs, etc. Well known dyes that can be used in the present invention include ethidium bromide, acridine orange, propidium iodide, DAPI, 9 amino acridine, ethidium bromide homodimer, asymmetric cyanine dyes (e.g., TOTO, YOYO) either homo- or heterodimers. The structure of asymmetric cyanine dyes is discussed in H. S. Rye et al., "Stable Fluorescent Complexes of Double-stranded DNA with bis-Intercalating Asymmetric Cyanine Dyes: Properties and Applications," 20 Nucleic Acids Research, No. 11, pp. 2803 (1992). The selected dye or dyes bind to the nucleotides stoichiometrically along the DNA sequence, i.e., the binding sites along the fragments are such that the total number of dye molecules along any length of DNA is linearly related to the number of base pairs forming the DNA. For example, under the staining protocol set forth below, the number of ethidium bromide molecules bound to a DNA fragment is stoichiometric and can be as high as one-half the number of bp's. See, e.g., C. R. Cantor et al., "Binding of Smaller Molecules to Nucleic Acids," in *Biophysical Chemistry, Part III: The Behavior of Biological Macromolecules*, p. 1252, W. H. Freeman and Company (1980).

One exemplary procedure (J. Sambrook et al., *Molecular Cloning*, Cold Spring Harbor Press (1989)) for staining with ethidium bromide is:

Add DNA sample to a solution containing 1–5 μg of ethidium bromide per mL of solution and TE 8.0 buffer.

A suitable buffer is available from GIBCO and is 10 mM Tris-HCL and 1 mM EDTA, pH 8.0. The reaction is complete in 5–10 minutes at room temperature.

The stained DNA fragments are now analyzed using sensitive fluorescence detection techniques to determine the fluorescence intensity from each fragment passing through a detection region and having a high resolution to distinguish adjacent fragment sizes. Theoretically, while only a single DNA piece of each size is needed to obtain the desired distribution analysis, a typical solution will be formed from many DNA pieces and an absolute DNA fragment size distribution is obtained.

It is well-known how to form a sequential flow stream of particles for use in a flow cytometer or similar sensitive fluorescence detection apparatus. See, e.g., U.S. Pat. No. 3,710,933, issued Jan. 16, 1973, to Fulwyler et al. and *Flow Cytometry and Sorting*, 2nd Ed., ed. M. R. Melamed et al., Wiley-Liss, New York, 1990, incorporated herein by reference. A dilute solution of the DNA fragments is formed to a low concentration effective to provide the fragments spaced apart in the flow stream so that only a single fragment is present in the excitation and detection volume. The solution of DNA fragments is then introduced within a laminar sheath flow stream for passage through the detection chamber for light excitation of one fragment at a time. The flow rates of the sample and the sheath are adjusted to maintain separation between particles and to provide the optimum time for each particle in the excitation source. An optimum time is determined from a consideration of laser intensity, analysis rate, detection sensitivity, and photostability of the bound dye. A suitable excitation source is selected to initiate fluorescence in the dye used to stain the DNA fragments. For example, an argon laser at 488 nm is effective to cause ethidium bromide to fluoresce in a band around 600 nm.

The sensitivity of conventional flow cytometry systems is improved by providing a small excitation volume, e.g., 10–20 μm diameter and 100 μm length, with a tightly focused laser beam. See, e.g., J. H. Hahn et al., "Laser-Induced Fluorescence Detection of Rhodamine-6G at $6 \times 10^{-15}$M" Appl. Spectrosc. 45:743 (1991) describing a probe volume of 11 pL, incorporated herein by reference. The small probe volume greatly reduces the amount of background emission, i.e., noise, in the output signal.

The laser excitation may be a pulsed laser with a pulse of e.g., about 70–200 ps full width, with time gating to differentiate between dye emission photons (delayed) and Raman and Rayleigh scattered photons (prompt). See, e.g., E. B.

Shera et al., "Detection of Single Fluorescent Molecules," Chem. Phys. Lett. 174:553 (November 1990) and C. W. Wilkerson, Jr. et al., "Detection and Lifetime Measurement of Single Molecules in Flowing Sample Streams by Laser-Induced Fluorescence," submitted to Appl. Phys. Lett. (September 1992). The prompt scattered photons occur during the laser pulse while the dye emissions decay with a several nanosecond lifetime so that a delayed detection window is effective for discrimination of fluorescence photons from Raman scatter photons. Alternatively, the laser may be a cw laser. See, e.g., S. A. Soper et al., "Single-Molecule Detection of Rhodamine-6G in Ethanolic Solutions Using Continuous Wave Laser Excitation," Anal. Chem. 63:432 (1991). The number of emitted photons can be increased by increasing the laser intensity, the DNA fragment transit time through the laser beam, and by selecting a dye and solvent with high photostability for the dye. The number of detected photons (photoelectrons) is also increased by increasing the sensitivity of the detection apparatus. Furthermore, since the present invention involves DNA fragments containing many dye molecules rather than a single molecule, a larger output fluorescence intensity is obtained.

It will also be appreciated that the solution may contain some dye that is not bound to the DNA fragments. This dye will be excited along with bound dye and in some cases the system must discriminate between the fluorescence from the unbound and the bound dye. In one embodiment, a pulsed laser and time gated detection technique may be used to provide this discrimination. For example, the excited state lifetimes for the unbound and bound ethidium bromide are 2 ns and 23 ns, respectively. Thus, the detection system can be gated to detect primarily the fluorescence from the bound ethidium bromide and, hence, provide an output signal functionally related to the length of the DNA fragment.

Alternatively, a dye might be selected that provides different fluorescence or absorption wavelengths in the bound and unbound states. For example, a series of asymmetric cyanine dyes are reported by I. D. Johnson et al., "Asymmetric Cyanine Dyes for Fluorescent Staining and Quantification of Nucleic Acids," Fluorescence Spectroscopy, Abstract 1806, FASEB J. 6:A314, No. 1 (January 1992). Another alternative might simply discriminate based on the greater fluorescence from the bound dye over the unbound dye. For example, the fluorescence enhancement of TOTO-1 upon binding is approximately 1000 (Rye et al., supra.).

The flow cytometry-type apparatus provides a high resolution to distinguish among fragments of similar lengths. Indeed, the resolution can be limited by shot noise in the photons arising from the fluorescence emissions and the percent resolution increases as the number of base pairs forming the DNA fragments increases. At some point instrument instabilities and techniques limit the resolution. In flow cytometry, resolution (CV) can be 0.1–1% when shot noise limit is exceeded.

Two quantities that are used to access the quality of an analysis are the accuracy (A) with which the mean can be determined and the resolution of coefficient of variation (CV), which is the standard deviation of a distribution divided by the mean of the distribution and is related to the band width. The accuracy (A) and resolution (CV) are determined by the length of the fragment (L), the fraction of the fragment tagged (f), the number of photoelectrons collected per tag (b) (b is typically about 30 for the apparatus described herein), and the number of times a given fragment type is sized (N). The mean intensity is given by $\mu$. The percent accuracy A at a standard deviation of $3\sigma$ is given by $$A(\%)=3*100N^{-1/2}*(L*f*b**)^{-1/2},$$

where $$\mu=L*f*b*; \sigma=\mu^{1/2}; \text{ and } CV=\sigma/\mu.$$

For example, consider the case of a fragment 1000 bases long: L=1000, f=0.5 (e.g., ethidium bromide; f=0.2 for TOTO), b=30. For N=1, $\mu$=15000, $\sigma$=122.47, A=2 45%, and CV=0.008. The accuracy improves as $N^{-1/2}$. Thus, for N=1000, $\sigma$=3.87 and A=0.0775%. Sizing 10, 100, or even 10,000 identical fragments is not a problem. There are many more fragments than 10,000 in a typical electrophoresis band. Thus, it can be seen that the accuracy can be much better than 1% on a 100,000 bp fragment, whereas an accuracy of only 10–20% would be expected for separation of fragments in the 100,000 bp range by gel electrophoresis and the accuracy and resolution degrades further as fragment length increases. It will be understood that the above analysis provides theoretical limits and instrumentation limitations may preclude the attainment of the theoretical limit.

DNA fingerprinting according to the present invention can also be done very rapidly. A typical DNA fingerprint by electrophoresis has about 50 bands. At 1000 fragments per band, 50 bands would require only about 17 minutes to develop a fingerprint at a fragment analysis rate of 50 fragments/second. If the desired resolution requires 100 fragments per band, then the 50 band analysis would take only about 100 seconds.

Experimental Results

Apparatus

FIG. 1A illustrates, in block diagram form, optics and electronics used for exciting and detecting fluorescence from a single, stained DNA fragment. Mode-locked laser 10 emits laser beam 12 that is passed through lens 22 into flow cell 24. A portion of beam 12 may be directed by beam splitter 14 to photodiode 16 for outputting a pulse train synchronous with the laser pulse train from mode-locked laser 10.

Laser beam 12 is focused by lens 22 into detection volume 26 within flow cell 24. As an extremely dilute solution of dye stained DNA molecules flows through detection volume 26, laser beam 12 induces the emission of fluorescence light from the dye molecules. Some of the laser light is also scattered from water in flow cell 24. To detect fluorescent output from detection volume 26, microscope objective 32 (which collects approximately 10% of the total light emitted from detection volume 26) collects fluorescent and scattered light 28 from detection volume 26 and images it on an opaque plate 30, which defines a slit. Only light that originates from detection volume 26 (about $10^{-12}$ liters), a small fraction of the water illuminated by beam 12, passes through the slit. This arrangement minimizes the passage of light that originates from sources other than substances in detection volume 26. Light emerging from the slit is spectrally filtered by filter 31 and focused by lens 34 upon the photocathode of photomultiplier 38, which outputs a pulse for each photon that generates a photoelectron at the photocathode (typically 15% of the photons striking the photocathode generate photoelectrons). The output from photomultiplier 38 is input to amplifier and discriminator 42 where signal pulses are amplified and those that exceed a threshold (chosen to eliminate electronics noise) cause a negative NIM pulse (an IEEE standard pulse for communicating between instruments) to be generated. This NIM pulse is synchronous to the input pulse and has an adjustable duration. The output pulse train from photodiode 16 is also conditioned with amplifier and discriminator 40 so that the resulting NIM pulse train is synchronous with the laser pulse train from laser 10.

The duration of the NIM pulse from laser amplifier/discriminator 40 is adjusted to about 5 nanoseconds. The width of the NIM pulse from photomultiplier amplifier/discriminator 42 is adjusted to approximately 10 nanoseconds. The photomultiplier NIM pulse train is delayed with respect to the laser NIM pulse train by adjustable (0–63 ns) delay line 43. The delayed photomultiplier NIM pulse train and the laser NIM pulse train are input to fast logic unit 44, which generates a negative logic NIM pulse only when overlapping (in time) NIM pulses are present at the inputs. Proper adjustment of the width and delay of the photomultiplier NIM pulse train with respect to the laser NIM pulse train results in fast logic unit output pulses for only delayed fluorescence. Prompt emission (primarily Raman and Rayleigh scatter from water in detection volume 26) does not give rise to output pulses from fast logic unit 44. The output pulses from fast logic unit 44 are counted by multi-channel scaler 46, the address of which is advanced by 10 kHz clock 45. Computer 50 receives the output from multi-channel scaler 46 to provide a record in time of the delayed fluorescence emitted from substances flowing through detection volume 26.

Figure 1B:
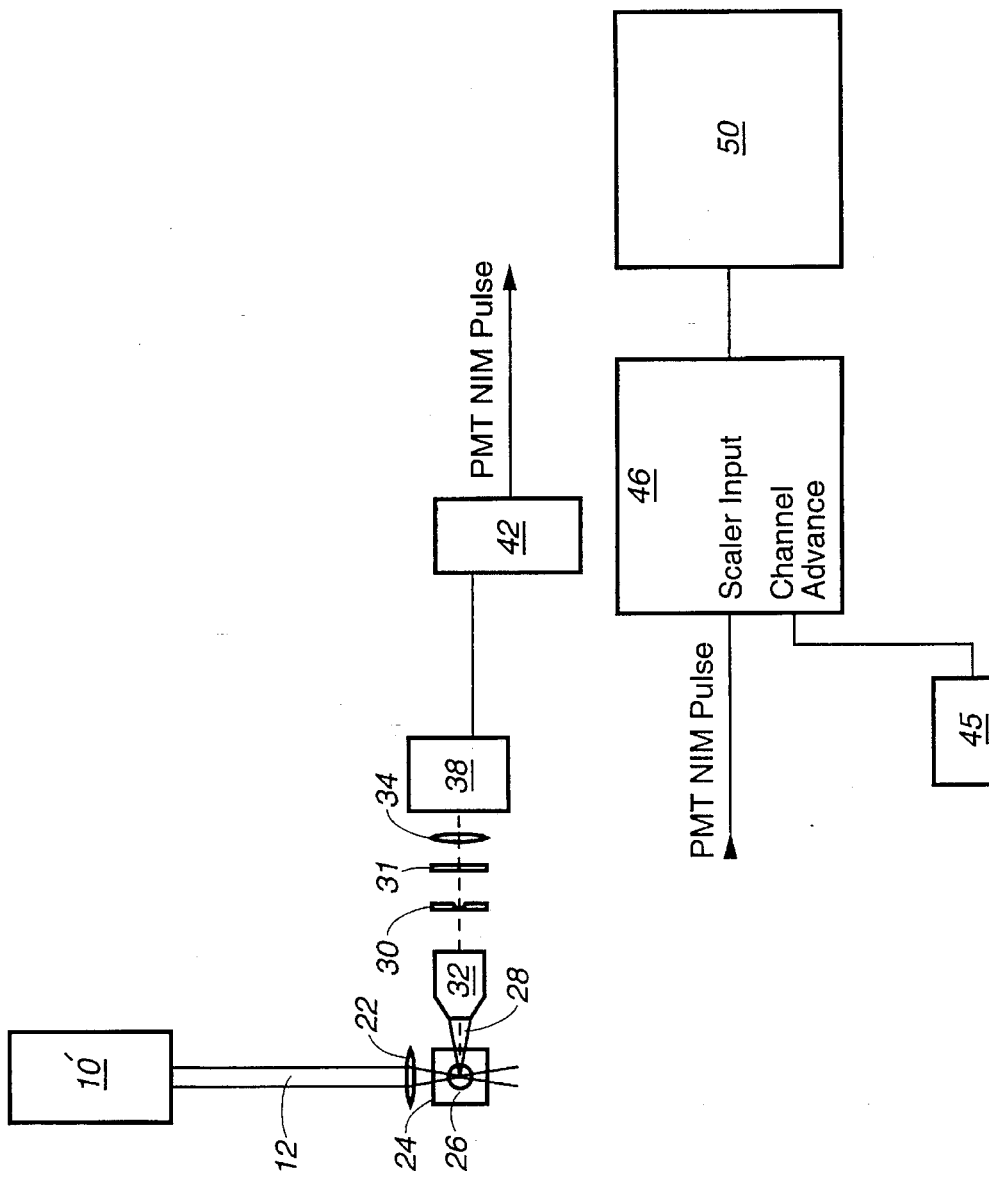
FIG. 1B is a block diagram schematic of apparatus for DNA sizing using continuous wave (cw) laser excitation.

FIG. 1B is a block diagram schematic of optics and electronics for a continuous wave laser beam excitation of a single, stained DNA molecule. Output 12 from CW laser 10' is directed through lens 22 into flow cell 24 within detection volume 26. Fluorescence output 28 from a stained DNA molecule within detection volume 26 is input to microscope objective 32. Fluorescence light 28 is imaged on an opaque plate 30 defining a slit. Light emerging from the slit is filtered by filter 31 and focused by lens 34 on the photocathode of photomultiplier 38. The output from photomultiplier 38 is input to amplifier and discriminator 42 to output NIM pulses.

The NIM pulses output from amplifier 42 are input to multi-channel scaler 46, which is clocked by 10 kHz clock 45. Channel outputs from scaler 46 are output to computer 50 to maintain a record of fluorescence emitted from excited molecules in detection volume 26.

Experimental Results

1. λDNA and KpnI digest of λDNA stained with TOTO-1:

Apparatus

As generally shown in FIG. 1B above, laser 10' provided thirty milliwatts of continuous wave Ar$^+$radiation at 514.5 nm. Beam 12 was focused to a beam waist of 40 μm (1/e$^2$ diameter) in the center of detection volume 26. Flow cell 24 was a modified commercial square bore sheath flow cuvette (Ortho Diagnostics, Inc., available from BDIS, Milpitas, Calif.) with a 250 μm internal cross section. The collection side was cut down to a microscope cover slip thickness to allow positioning of microscope objective 32 at its working distance from the sample stream. Light collected by microscope objective 32 (40×, 0.85 NA), is spectrally filtered (detection bandwidth 520–545 nm) to remove Raman and Rayleigh scattering from the water solvent and spatially filtered by the slit defined by opaque plate 30. The spectral filter 31 consisted of two elements: a Raman holographic edge filter with a specified optical density (OD)>4.5 at 514.4 nm and, an OD<0.3 for wavelengths longer than 520 nm (RHES514.5 nm, Physical Optics Corporation, Torrance, Calif.); and a bandpass filter with a 30 nm bandpass centered at 530 nm (530DF30, Omega Optical Inc., Brattleboro, Vt.) Photomultipler tube 38 outputs a signal to amplifier and discriminator 42 that is counted by multichannel scaler 46.

Sample

A mixture of λDNA (GIBCO/BRL, Gaithersberg, Md.) and KpnI digest of λDNA (New England Biolabs, Beverly, Mass.) containing fragments of length about 50 kbp or less 148,502 bp; 29,945 bp: 17,053and 1,503 bp in this example) was stained stoichiometrically with the DNA intercalating dye TOTO-1 (a thiozol orange dimer from Molecular probes, Eugene, Oreg.). The λDNA and KpnI digest of λDNA were stained separately at a DNA concentration of 400 pg/μl. The TOTO-1 concentration was $1.2\times10^{-7}$M to yield an average bp:dye ratio of 5. The sample mixture was prepared by adding equivalent aliquots of each stained DNA solution to buffer diluent for a final total fragment concentration of approximately $10^{-13}$M, i.e., about 3 ng/ml of DNA. All solutions were prepared in pH 8 TE buffer (10 mM Tris-HCl, 1 mM EDTA).

Flow Cytometry

Within detection volume 26, the sheath fluid was water. Sheath flow was produced by gravity feed at a flow rate of about 30 μl/min. The sample flow was also produced by gravity flow at rates below 1 μl/min. Flowing, fluorescently stained fragments were hydrodynamically focused in detection volume 26 at a rate of about 50 fragments per second (velocity of about 3.7 cm/sec.), which provided a probability of two fragments in the probe volume at the same time of about 5%. The focused sample stream diameter was about 20 μm at the center of a 250 μm square bore flow chamber.

Fluorescence from the intercalated dye was collected by microscope objective 32 and spectrally filtered 31 to remove Raman and Rayleigh scattering from the water solvent (detection bandwidth 520–545 nm), spatially filtered by the slit defined by opaque plate 31 to define output from detection volume 26, and focused upon the photocathode of photomultiplier tube 38.

Photoelectron pulses from photomultiplier 38 were processed through amplifier/discriminator 42, counted by multichannel scaler (MCS) 46, and output to computer 50 for analysis. The MCS that counted photoelectrons was advanced by clock 45 that ran at 10 KHz (100 μs bins). The raw MCS data stream was sifted for bursts in the following manner. The average background fluorescence rate was determined from the data during quiescent periods between fluorescence bursts. Contiguous (in time) data points above a predetermined threshold were accumulated, after subtraction of background, to give the burst size in photoelectrons (PE). The average background fluorescence rate for the data shown in FIG. 2 was 16 PEs per bin; the threshold was set at 20 PEs per bin.

Data Processing

Figure 2:
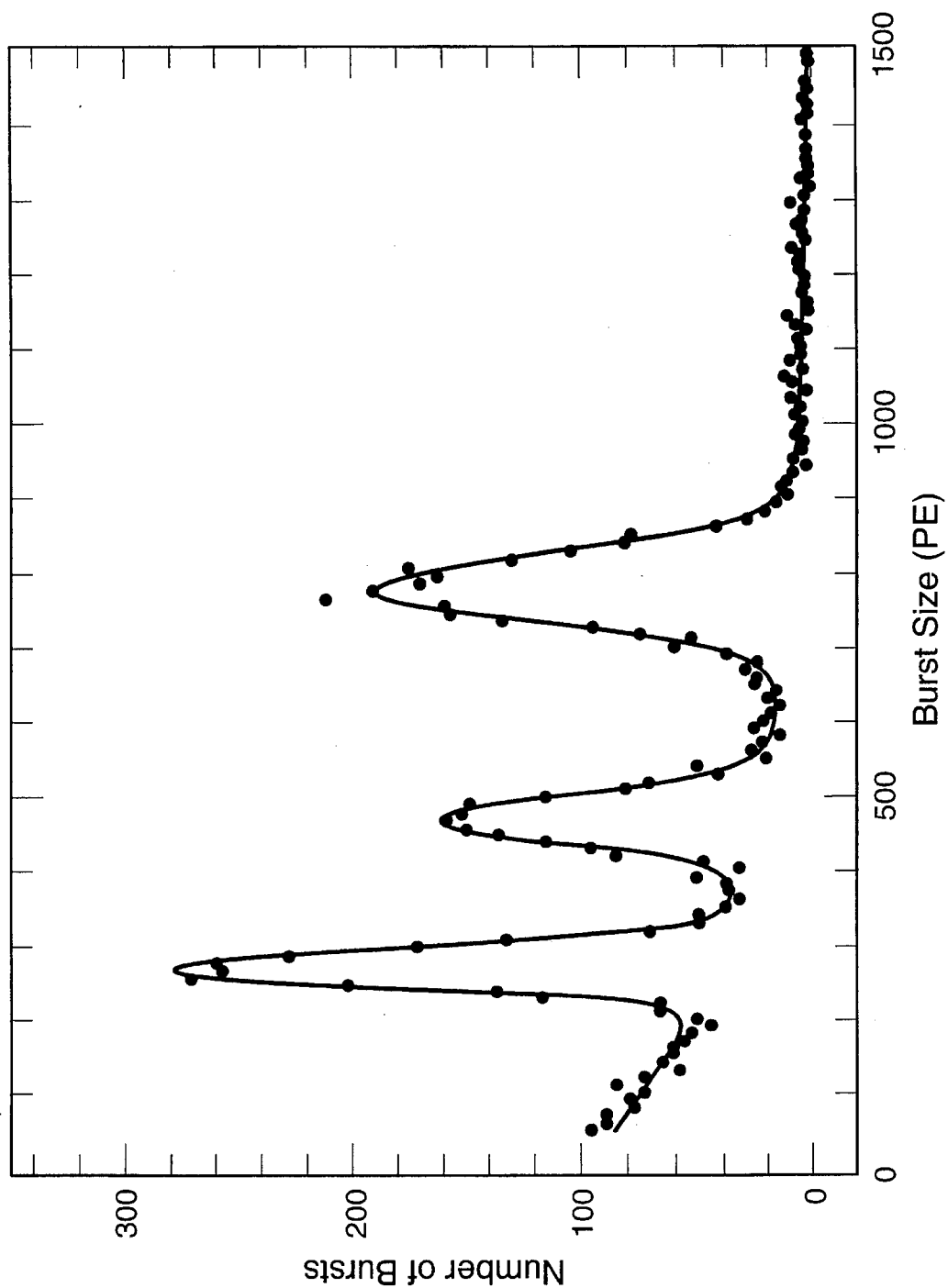
FIG. 2 graphically depicts a histogram of the fluorescence burst sizes from a mixture of λDNA and KpnI digest of λDNA containing fragment sizes of 48,502 bp; 29,946 bp; 17,053 bp; and 1,503 bp. The signature of the fragment length of 1,503 bp is masked by background fluorescence. The DNA was stained with TOTO-1 and the excitation was with a cw laser.

After subtraction of background counts, the data were screened for photon bursts greater than the specified threshold amount. FIG. 2 presents graphically a histogram of the analysis of 164 seconds of data containing measurements of about 8000 DNA fragments. Peaks corresponding to the 48, 30, and 17 kbp fragments are well resolved. Signals from the 1.5 kbp fragment are masked by background scatter and impurity fluorescence. Centroids of the peaks in FIG. 2 were obtained by fitting the data to the sum of three Gaussians plus an exponential background. The fitted curve is also shown in FIG. 2.

Figure 3:
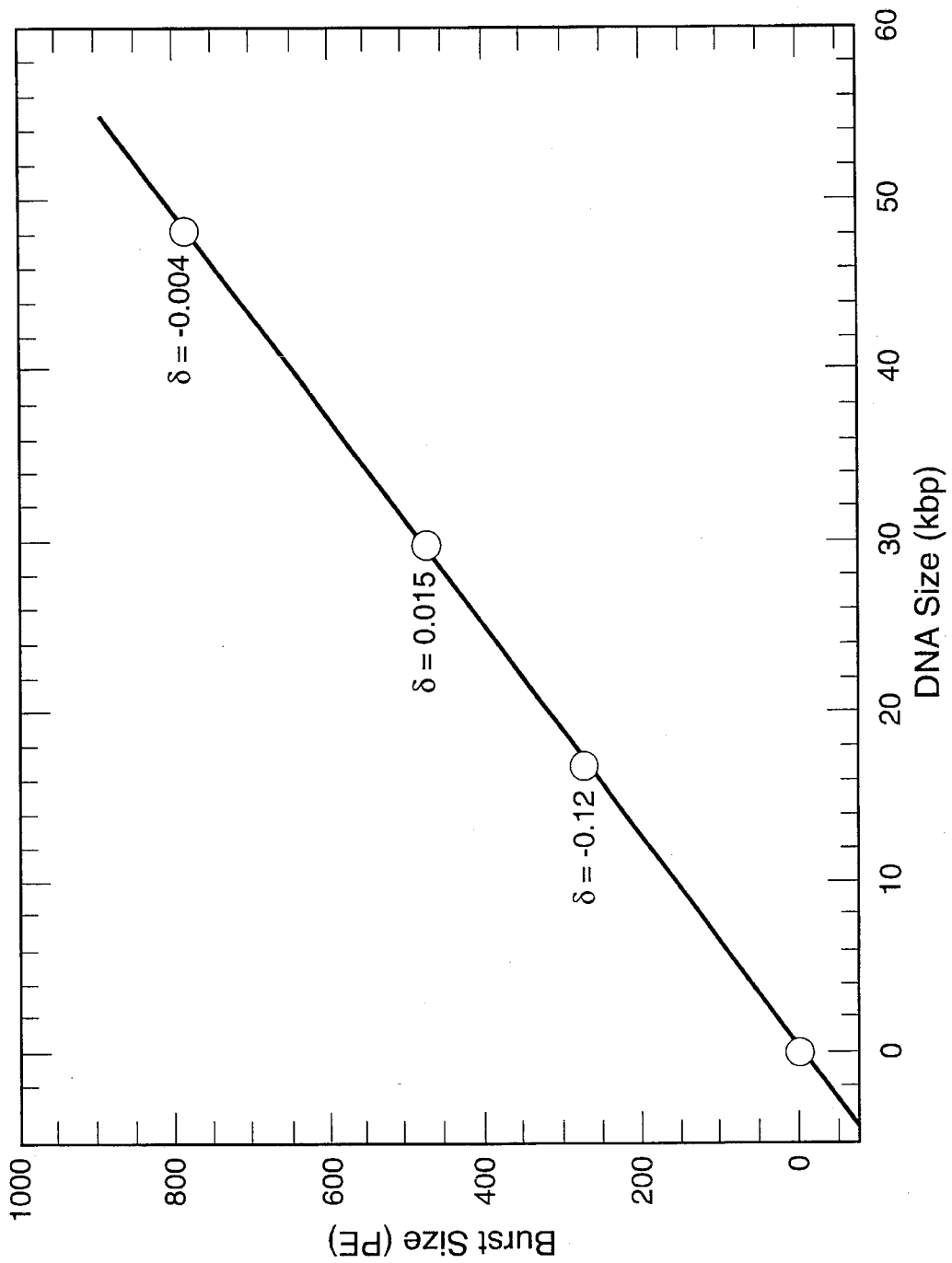
FIG. 3 graphically depicts the correlation of the centroids of the measured burst sizes with known DNA fragment lengths for the data shown in FIG. 2, with the correlation having correlation coefficient R=0.99986 for the linear regression fit.

FIG. 3 illustrates graphically a plot of the centroids of the burst size peaks versus the known DNA fragment lengths in the sample mixture. The origin point (0,0) is included in the fit, which has a correlation coefficient R=0.99986. The linearity of this fit including the origin indicates that the DNA fragments were stoichiometrically stained by the TOTO-1 dye.

2. λDNA and ApaI digested λDNA

Figure 4:
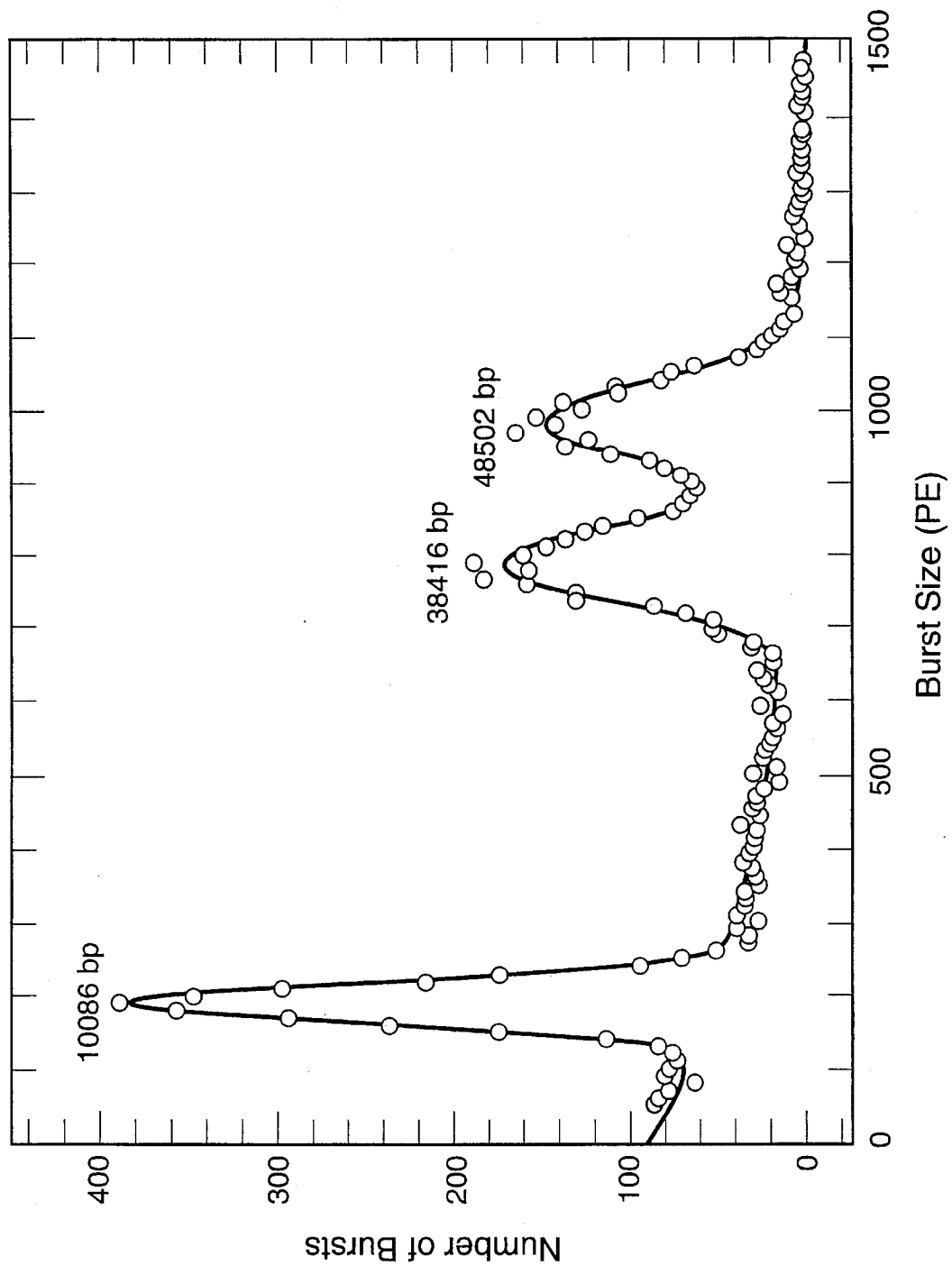
FIG. 4 graphically depicts a histogram of the fluorescence burst sizes from a mixture of λDNA and ApaI digest of λDNA containing fragment sizes of 48,502 bp; 38,416 bp; and 10,086 bp. The DNA was stained stoichiometrically with TOTO-1 and the excitation was with a cw laser.

This experiment was identical to Experiment 1 above except that a mixture of ApaI digested λDNA (New England Biolabs, Beverly, Massachusetts) and λDNA was used to form the sample with fragment lengths of 48,502 bp; 38,416 bp; and 10,086 bp. The fragments were again stained with TOTO-1 with a bp:dye ratio of 5. As seen in FIG. 4, the fragment lengths are readily resolved by flow cytometry. A graph similar to FIG. 3 shows stoichiometric staining over the range of fragment lengths.

3. λDNA and KpnI digested λDNA stained with ethidium homodimer (EthD)

The equipment and procedure for Experiment 1 were used except that the equipment was a mode-locked laser system as described for FIG. 1A and the stain was the intercalating dye ethidium homodimer.

Sample

The sample was prepared as follows:
a. The commercial DNA solutions (both λDNA and KpnI digested λ DNA) were diluted to a concentration of approximately 5 µg/ml.
b. A dilute EthD dye stock solution was prepared by diluting commercially obtained EthD by a factor of 90 for a final concentration of 10 µg/ml.
c. An equilibrium staining solution was formed by pipetting 81.0 µl of the dilute DNA solution, above, into 892 µl of buffer (pH 8 TE), mixing, and adding 26.6 µl of the above dilute EthD stock solution. The resulting concentration of the DNA fragments in the solution was 400 ng/ml or $1.25 \times 10^{-11}$M.
d. The mixture was incubated in the dark at room temperature for 1 to 1½ hours.
e. The solution for analysis was prepared by pipetting 11.1 µl of the incubated solution into 1474 µl of buffer for a final DNA concentration of $1 \times 10^{-13}$M.

Flow Cytometer

Same as Experiment 1, above, with a sheath flow rate of 25 µl/min and a sample flow rate of 0.2–1.0 µl/min focused to a 20 µm sample stream diameter.

It was necessary to operate with mode-locked laser excitation, operating at 82.5 MHz with 200 picosecond pulses at 100 mW, 514 nm, due to the reduced signal and increased water Raman background present in the spectral detection band.

Figure 5:
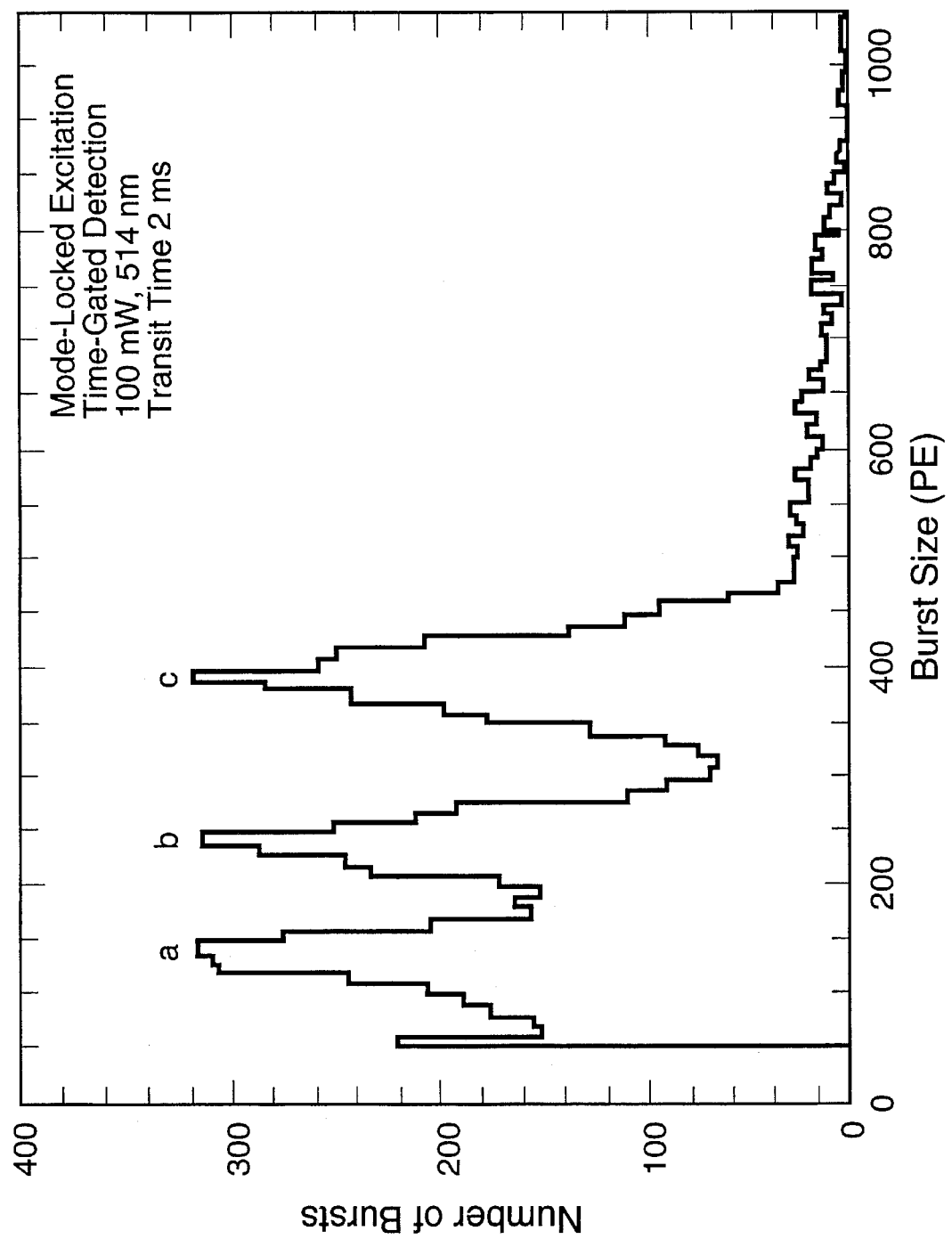
FIG. 5 graphically depicts a histogram of the fluorescence burst sizes from λDNA and KpdI digest of λDNA stained with ethidium homodimer under pulsed excitation and time gated detection.
Figure 6:
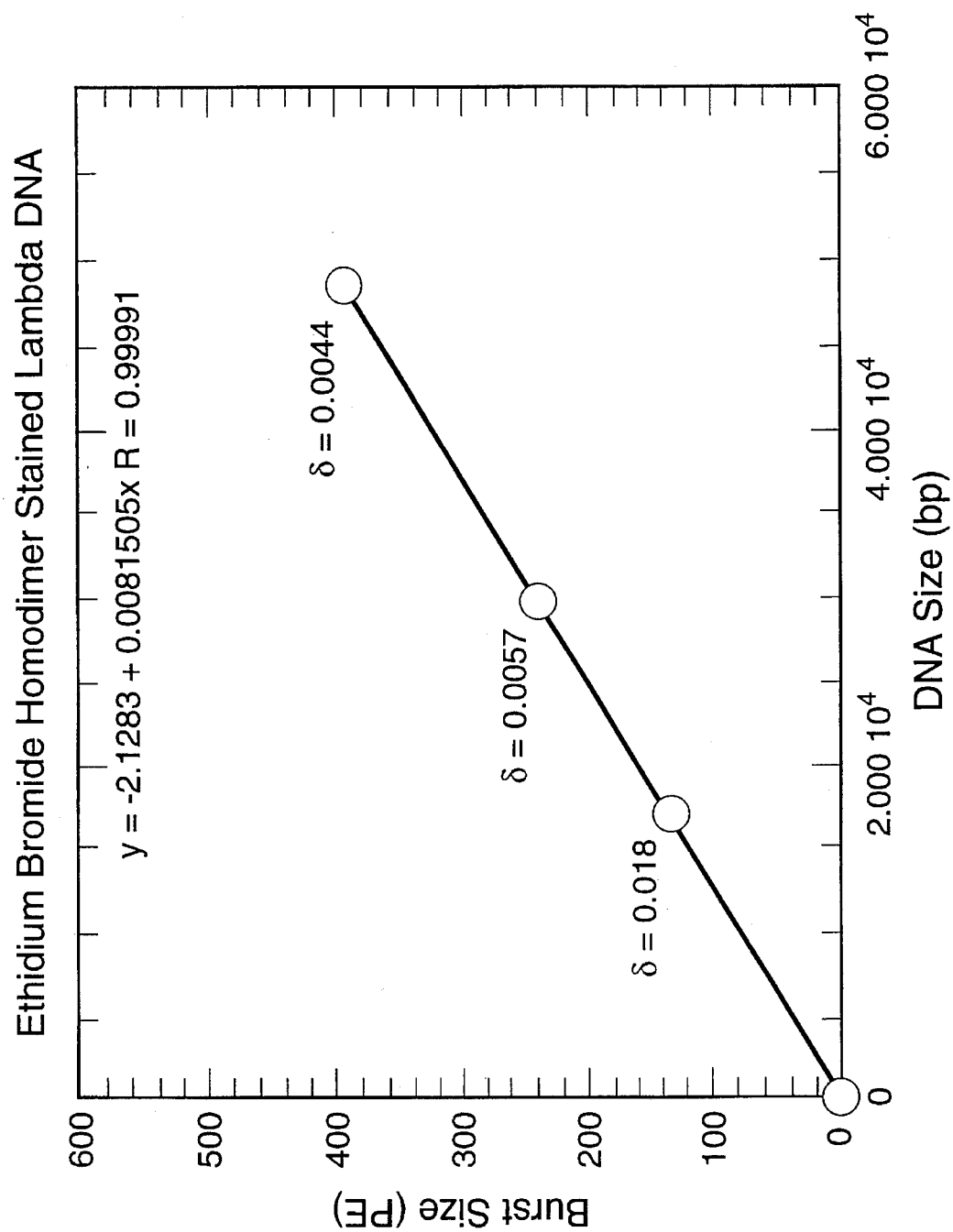
FIG. 6 graphically depicts the correlation of the centroids of the measured burst sizes with the known DNA fragment lengths for the data shown in FIG. 5, with the correlation having a correlation coefficient of R=0.99991 for the linear regression fit.

FIG. 5 presents a histogram of the measured burst sizes with peaks corresponding to the DNA fragment sizes of 48 kbp, 30 kbp, and 17 kbp. The 1.5 kbp length was again not resolved because of background fluorescence and/or scatter. A curve was fit to the raw data, as in Experiment 1, and the burst size peaks were correlated with fragment length. This correlation is shown in FIG. 6. A linear fit was made to the data and included the origin with a correlation factor of R=0.99991. Again, the dye stained the DNA fragments stoichiometrically.

4. λDNA and KpnI and ApaI digested λDNA

The equipment was the cw laser shown in FIG. 1B and used in example 1 above. The λDNA and KpnI and ApaI digested λDNA were stained separately with TOTO-1 dye at a DNA concentration of 400 pg/µl using the procedure of example 1. The resulting sample included fragment lengths of 48,502 bp; 38,416 bp; 29,946 bp; 17,053 bp; 10,086 bp; and 1,503 bp.

Figure 7:
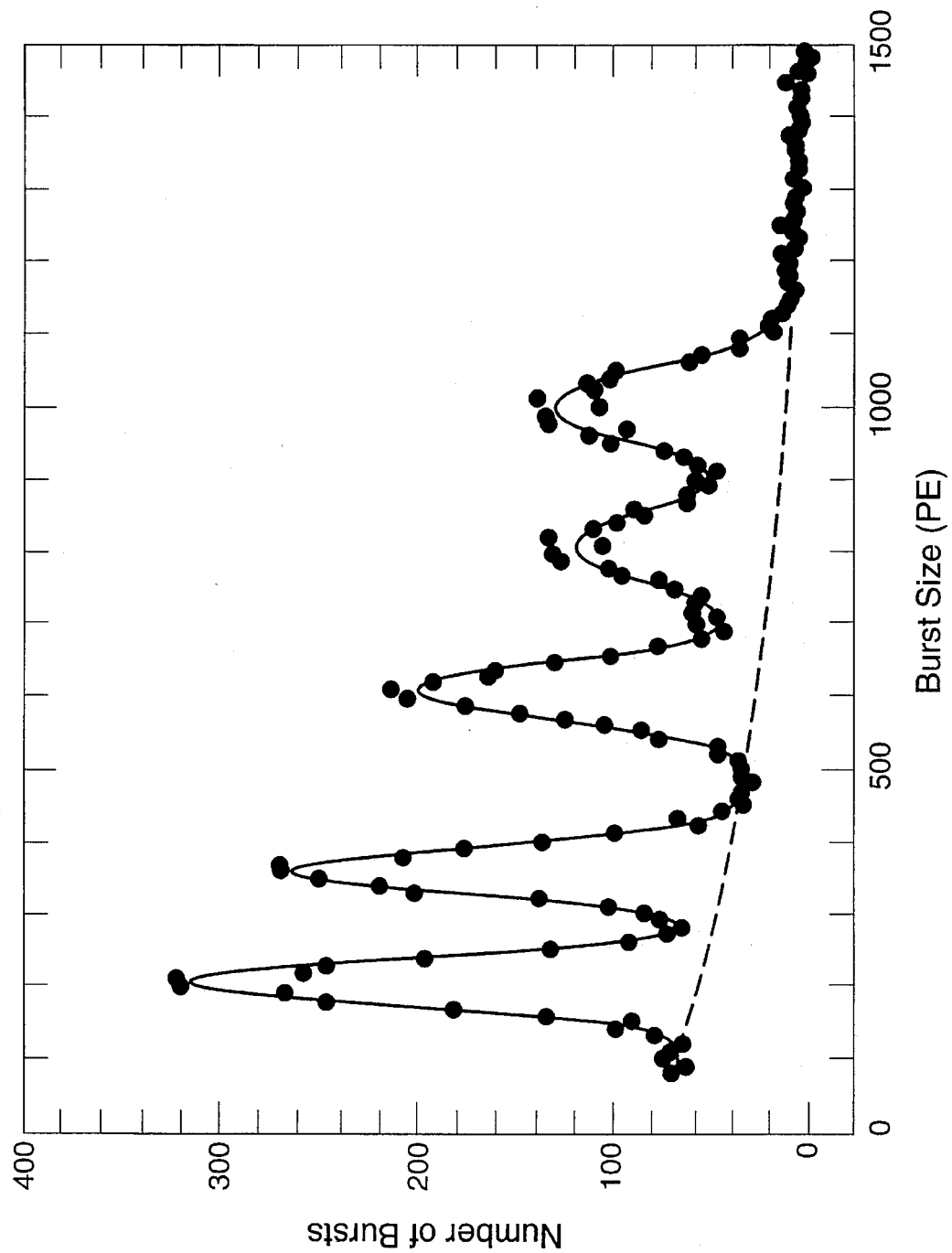
FIG. 7 graphically depicts a histogram of the fluorescence burst sizes from a mixture of λDNA, a KpnI digest of λDNA, and an ApaI digest of λDNA containing fragment sizes of 48,502 bp; 38,416 bp; 17,053 bp; 10,086 bp; and 1,503 bp stained with TOTO-1 under cw excitation. The signal from the 1,503 bp fragment was masked by the background signal.
Figure 8:
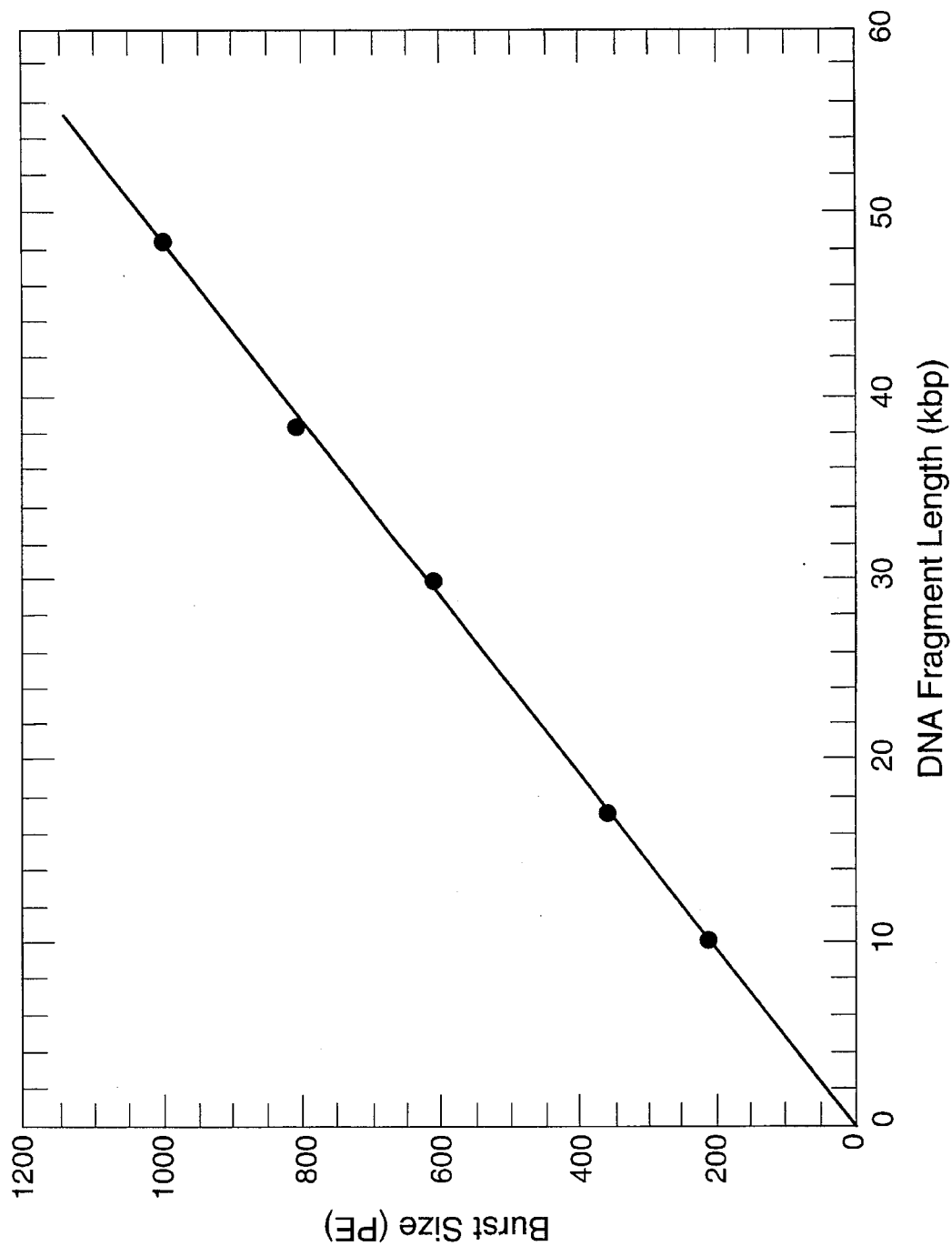
FIG. 8 graphically depicts the correlation of the centroids of the measured burst sizes with known DNA fragment lengths for the data shown in FIG. 7, with the correlation having a correlation coefficient of R=0.9996 for the linear regression fit.

The sample was analyzed using the flow cytometry and data processing procedures of example 1. FIG. 7 is a histogram of the sample fluorescence burst sizes with a solid line fit to the data. The dashed line is the exponential fit to the underlying background fluorescence. FIG. 8 is the correlation of the centroids of the measured burst sizes with known DNA fragment lengths. The correlation coefficient for the linear regression fit is R=0.9996 with the line passing through the origin within the error of the fit.

The resolution of the data obtained in example 4 can be represented by the coefficient of variation of the individual separated peaks in the histogram, as set out in Table A. As shown in Table A, the CV is similar to the resolution available from gel electrophoresis at 40 kb (CV=0.05 from flow cytometry sizing and CV=0.04 from gel electrophoresis as calculated from data presented in H. R. Reese et al., 92 J. Chem. Phys. 2650 (1990)).

TABLE A

| Fragment Size (bp) | Burst Centroid (PE) | A % | CV | √n/n |
|---|---|---|---|---|
| 10086 | 210.8 | 0.016 | 0.137 | 0.068 |
| 17053 | 364.8 | −0.017 | 0.084 | 0.053 |
| 29946 | 614.8 | 0.017 | 0.063 | 0.041 |
| 38416 | 813.0 | −0.016 | 0.064 | 0.035 |
| 40000* | | | 0.04 | |
| 48502 | 1004.1 | 0.005 | 0.050 | 0.032 |

* - gel electrophoresis data

5. KpnI digested λDNA—high resolution

The sample was prepared and analyzed using the flow cytometry and data processing procedures of Example 1, except that three parameters were adjusted to optimize the resolution for the smallest DNA fragment size, i.e., the 1,503 kbp size. In particular, the bandpass center of the fluorescence detection filter was increased from about 530 nm to about 550 nm to improve the signal-to-noise ratio of the detected signal. Further, the laser power was increased to 70 mW and the fragment transit time in the fluorescence detection volume is increased from about 1 ms to 4.6 ms by reducing the sample flow rate held to about 0.2 µl/min. These changes provide an increased number of photoelectrons from the laser excitation.

Figure 9A:
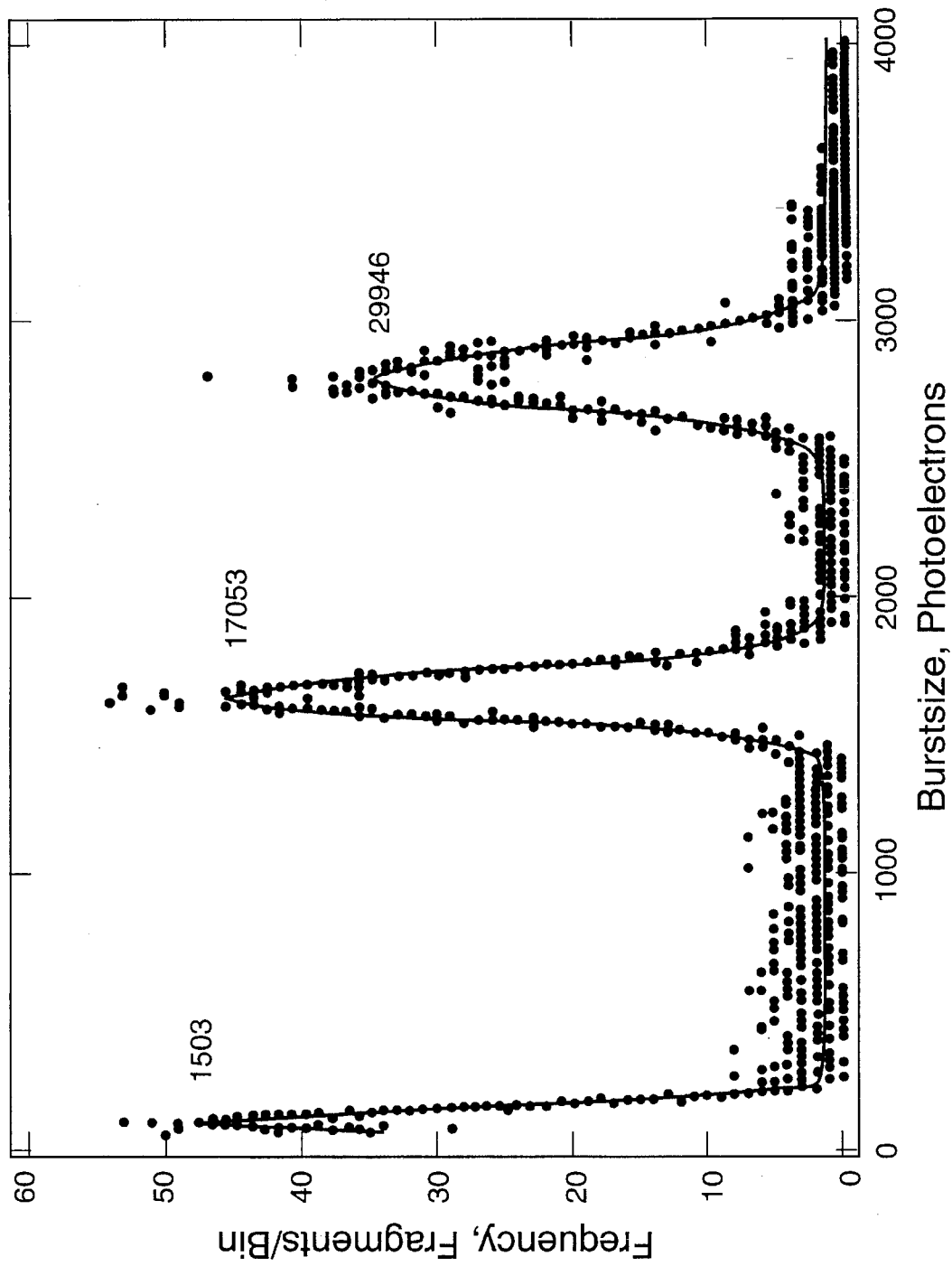
FIGS. 9A and 9B graphically depict histograms of the fluorescence burst sizes from TOTO-1 stained KpnI digest of λDNA containing fragment sizes of 29,946 bp, 17,053 bp, and 1,503 bp with enhanced resolution detection.
Figure 9B:
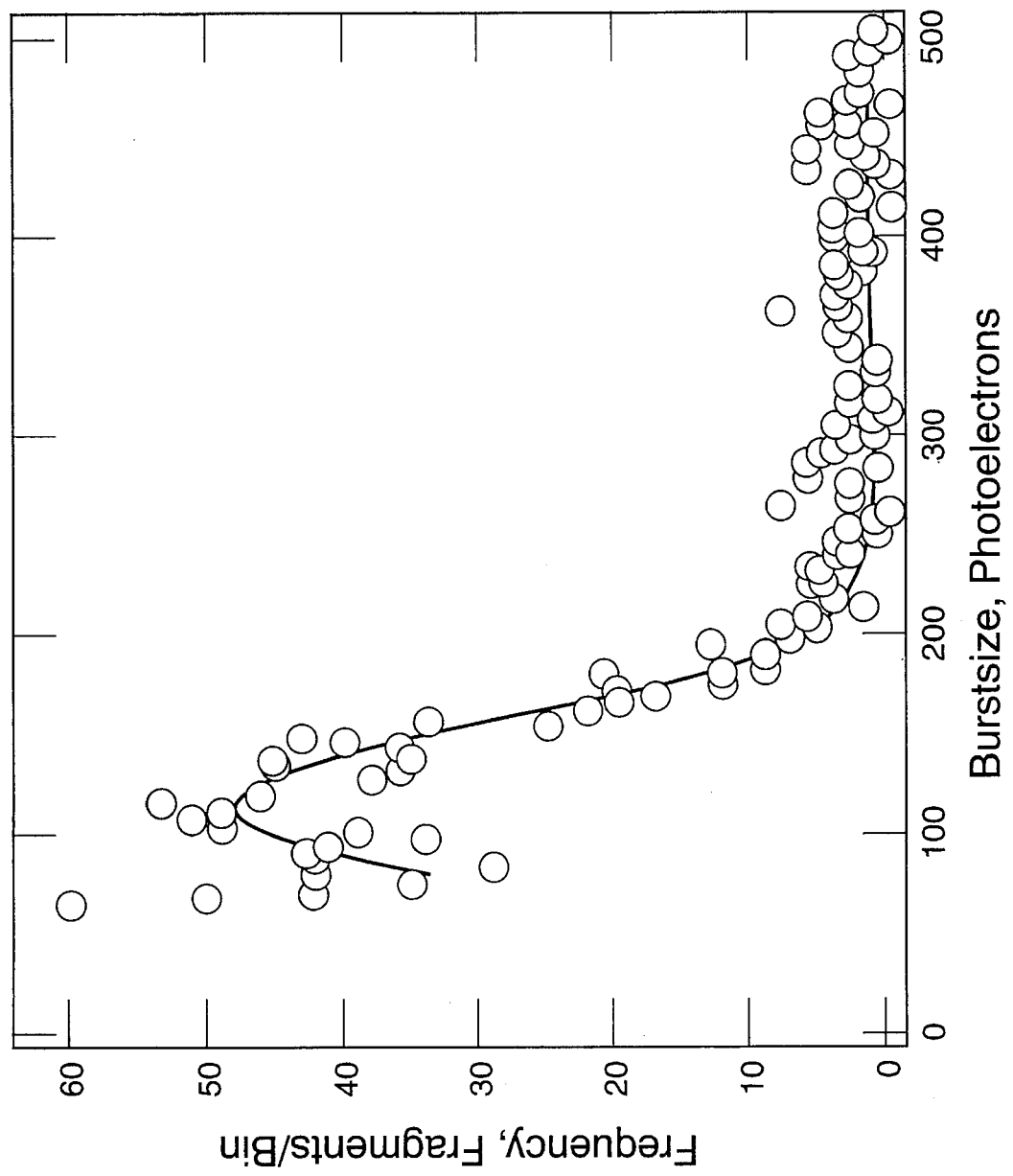

FIGS. 9A and 9B show the histograms for the number of bursts detected as a function of burst size, i.e., number of photoelectrons detected, for each fragment size. FIG. 9B is an enlarged histogram of the data obtained around the 1,503 bp fragment size. The centroid of the 1,503 bp peak was readily determined using the algorithm described for FIGS. 2 and 3.

Figure 10:
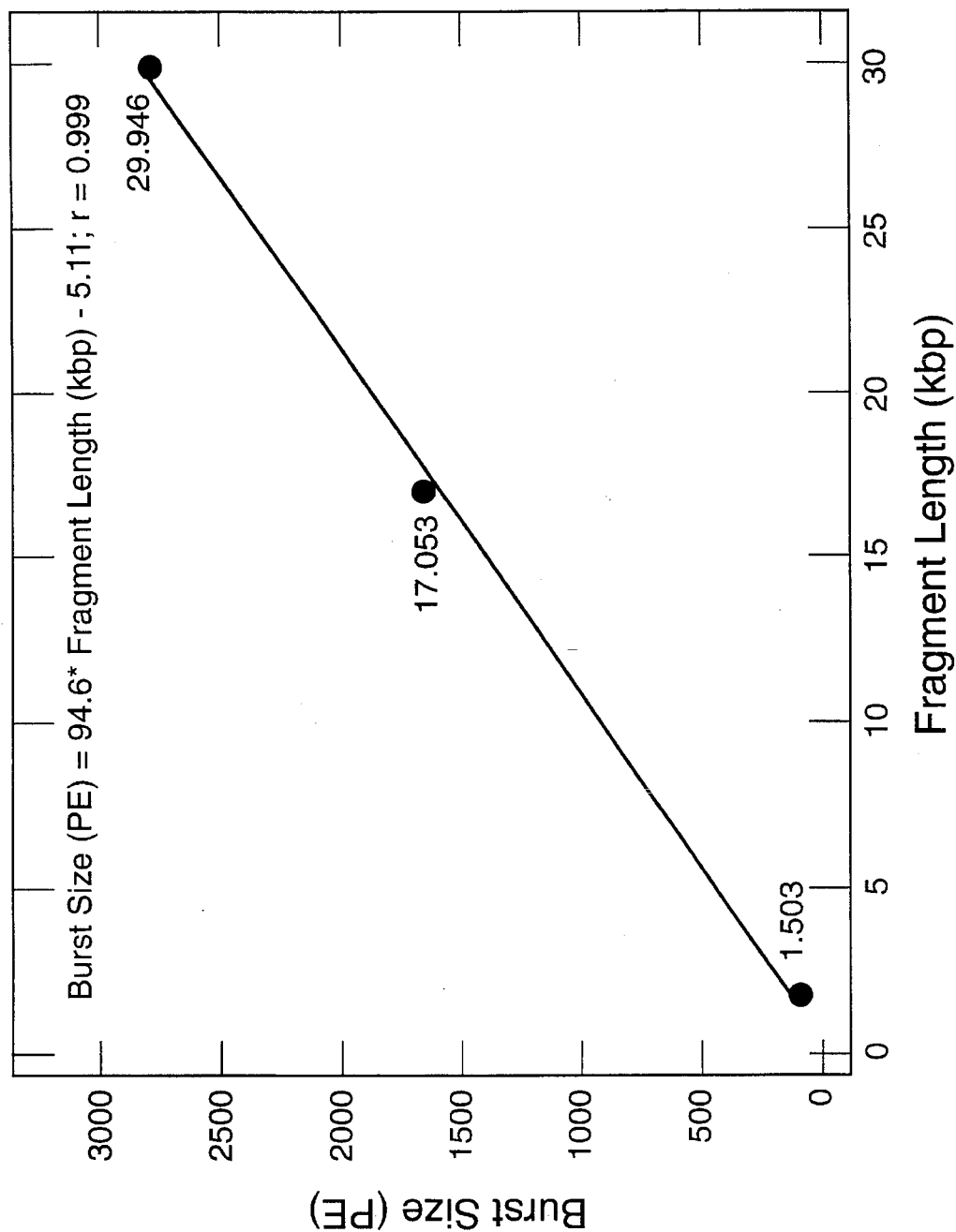
FIG. 10 graphically depicts the correlation of the centroids of measured burst sizes with known DNA fragment lengths for DNA fragment sizes of 1.503 kbp, 17.053 kbp, and 29.946 kbp with a correlation coefficient of R=0.999 for a linear regression fit.

FIG. 10 graphically depicts the resolution for fragment sizes of lengths 1,503, 17,053, and 29,946 bp. As shown in FIG. 10, the photoelectron burst size resolved for 1.503 kbp is on the linear regression line extending from the origin through the actual data points. It is expected that similar equipment and process modifications would enable the resolution of DNA fragments in the 1.5 kbp size range for all of the above examples.

Thus, the sensitivity of the system is readily enhanced by changes in operating parameters that are well within the skill of a person knowledgeable in flow cytometry. Indeed, a resolution down to a fragment size containing one dye molecule, i.e., 5 bp with TOTO-1, may be obtained using the techniques described in Wilkerson, Jr., supra, and Soper, supra. These resolution enhancements could be applied to Examples 1–4, above, and would be expected to enable the resolution of DNA fragments in the 1.5 kbp and smaller size range.

Thus, a process has been demonstrated for rapidly sizing DNA fragments from a mixture of fragments obtained by digesting large DNA fragments into smaller fragments. The fragment size distribution provides a characterization of the DNA that is useful in medical diagnostics and forensic studies.

An additional capability of the system can be provided by using various sorting systems associated with flow cytometers. See, e.g., U.S. Patent 3,710,933,supra, and *Flow Cytometry and Sorting*, supra. A sorting capability would enable one or more fragment sizes to be sorted from the flow stream for additional processing or study.

Conventional sorting apparatus, as discussed in U.S. Pat. No. 3,710,933 and in T. Lindmo, "Flow Sorters for Biological Cells," *Flow Cytometry and Sorting,Second Edition*, Ed. M. Melamed et al., pp. 145–169, John Wiley & Sons (1990), uses the fluorescence output signals discussed above. After the fragments have passed through the excitation/detection volume for generating the output, the hydrodynamic flow stream is broken into droplets by, e.g., ultrasonic vibrations, where each drop contains no more than one fragment. Drops containing DNA fragments that have a selected fluorescence response to an excitation are charged by the application of a high voltage pulse across the drops, which then pass between charged plates that generate an electrostatic field to selectively deflect the charged drops. The charge applied to the selected drops is controlled by circuitry that is responsive to fluorescent emissions from the excitation/detection volume within the flow cytometer, where the charging pulse is activated to produce a deflection of drops containing a material emitting fluorescence at a selected wavelength and intensity.

The above examples use lasers as the excitation source. However, any light source may be used that causes the excited material to fluoresce. Likewise, the form of signal detected is taught to be fluorescence. However, any form of light emission may be obtained, depending on the specific dye, such that the term fluorescence should be interpreted to include phosphorescence and luminescence. Further, the DNA being sized may not necessarily be from humans, since all organisms have a genome that determines their specific characteristics.

The foregoing description of the preferred embodiments of the invention have been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for quantitatively determining the number of nucleotides in DNA fragments of about 50 kbp or less, naturally occurring or obtained by fragmenting a larger piece of DNA at known sites within said piece of DNA by induced fluorescence, comprising the steps of:

staining said piece of DNA or said DNA fragments with a single dye effective to form stoichiometrically stained DNA or DNA fragments;

forming a flow stream of said stained DNA fragments serially spaced apart in said flow stream;

illuminating said flow stream with a light effective to cause said dye to fluoresce;

measuring the intensity of the fluorescence from each one of said stained fragments of DNA in said flow stream, wherein said intensity of said fluorescence is linearly related to said number of nucleotides in said stained DNA fragments Of about 50 kbp or less.

2. A method according to claim 1, wherein the step of staining said DNA piece or said DNA fragments with a dye includes the step of adding said DNA piece or said DNA fragments to a solution containing a dye selected from the group consisting of ethidium homodimer, asymmetric cyanine homo- and heterodimers, ethidium bromide, acridine orange, propidium iodide, 9 amino acridine, and ethidium acridine heterodimer.

3. A method according to claim 1, wherein said step of measuring said fluorescence intensity further includes the step of differentiating dye molecules bound to said DNA fragments from unbound dye molecules.

4. A method according to claim 1, wherein said step of illuminating said flow stream with a light includes the step of illuminating said flow stream with a pulsed laser.

5. A method according to claim 1, wherein said step of illuminating said flow stream with a light includes the step of illuminating said flow stream with a cw laser.

6. A method according to claim 1, wherein the step of measuring the intensity of said fluorescence includes the step of gating detection electronics to measure fluorescence at a predetermined time after said pulsed laser is initiated.

7. A method according to claim 1, wherein the step of staining said piece of DNA or said DNA fragments includes the step of adding said piece of DNA or said DNA fragments to a solution containing an intercalating dye.

8. A method for quantitatively determining the number of nucleotides in DNA fragments containing 50 kbp or less of nucleotides, naturally occurring or obtained by fragmenting a larger piece of DNA at known sites within said piece of DNA by induced fluorescence, comprising the steps of:

staining said piece of DNA or said DNA fragments with a single dye effective to form stoichiometrically stained DNA or DNA fragments;

forming a flow stream of said stained DNA fragments serially spaced apart in said flow stream;

passing said flow stream through an excitation and detection volume effective to contain only a single DNA fragment at a time;

illuminating said flow stream with a light effective to cause said dye to fluoresce;

counting the number of photons emitted by said dye to output a fluorescence signal from each one of said stained fragments of DNA in said flow stream; and determining a centroid value for each peak of said fluorescence signal, wherein said centroid value is linearly related to said number of nucleotides in each one of said stained DNA fragments having 50 kbp or less of nucleotides.

9. A method according to claim 8, wherein the step of passing only a single DNA fragment at a time through a flow volume includes the steps of:

providing a small excitation volume;

forming a flow stream with a selected velocity effective to retain said single DNA fragment in said excitation volume for a time effective to optimize said fluorescence from said DNA fragment; and providing said DNA fragments at a concentration wherein only a single DNA fragment is within said excitation volume at said selected velocity.

10. A method according to claim 8 wherein said step of illuminating said flow stream with a light includes the step of illuminating said flow stream with a pulsed laser.

11. A method according to claim 10, wherein the step of counting said number of photons includes the step of gating detection electronics to count said photons at a predetermined time after said pulsed laser is initiated.

12. A method according to claim 8, wherein said step of illuminating said flow stream with a light includes the step of illuminating said flow stream with a cw laser.

* * * * *